United States Patent
Ikuma et al.

(10) Patent No.: US 7,774,045 B2
(45) Date of Patent: Aug. 10, 2010

(54) MEDICAL GUIDING SYSTEM, MEDICAL GUIDING PROGRAM, AND MEDICAL GUIDING METHOD

(75) Inventors: Soichi Ikuma, Hachioji (JP); Tomonao Kawashima, Hachioji (JP); Masahiko Komuro, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 494 days.

(21) Appl. No.: 11/821,727

(22) Filed: Jun. 25, 2007

(65) Prior Publication Data
US 2007/0299336 A1 Dec. 27, 2007

(30) Foreign Application Priority Data
Jun. 27, 2006 (JP) .............................. 2006-177191

(51) Int. Cl.
A61B 5/05 (2006.01)
A61B 8/00 (2006.01)
(52) U.S. Cl. ...................................... 600/424; 600/439
(58) Field of Classification Search ................. 600/407, 600/424, 425, 437
See application file for complete search history.

(56) References Cited

U.S. PATENT DOCUMENTS 6,236,875 B1 * 5/2001 Bucholz et al. ............. 600/407

FOREIGN PATENT DOCUMENTS

| EP | 1 523 951 A2 | 4/2005 |
|---|---|---|
| JP | 10-151131 | 6/1998 |
| JP | 2002-345725 | 12/2002 |
| JP | 2004-113629 | 4/2004 |
| JP | 2005-312770 | 11/2005 |
| WO | WO 96/11624 | 4/1996 |
| WO | WO 2005/104955 | 11/2005 |

\* cited by examiner

*Primary Examiner*—Eric F Winakur
*Assistant Examiner*—Michael T Rozanski
(74) *Attorney, Agent, or Firm*—Scully, Scott, Murphy & Presser, P.C.

(57) ABSTRACT

The invention provides a medical guiding system including: a position data calculating device for detecting position and orientation of an ultrasonic endoscope serving as a medical instrument; image storing section for storing medical image data obtained before use of the ultrasonic endoscope; a body position correcting section for correcting at least one of position and direction at least one of viscera and organ in the medical image data, in line with a body position of the subject; and an image configuring section for calculating a position of the ultrasonic endoscope in the medical image data corrected by body position correcting section, based on a position of the ultrasonic endoscope obtained by the position data calculating device.

10 Claims, 7 Drawing Sheets

FIG.8A
REFERENCE IMAGE
SUPINE POSITION

FIG.8B
SUBJECT

FIG.8C
REFERENCE IMAGE
LEFT LATERAL POSITION

FIG.8D
SUBJECT

MEDICAL GUIDING SYSTEM, MEDICAL GUIDING PROGRAM, AND MEDICAL GUIDING METHOD

CROSS REFERENCE TO RELATED APPLICATION

This application claims benefit of Japanese Application No. 2006-177191 filed in Japan on Jun. 27, 2006, the contents of which are incorporated by this reference.

BACKGROUND OF THE INVENTION

1. Field of the Invention

The present invention relates to a medical guiding system, a medical guiding program, and a medical guiding method, for guiding a medical instrument using a medical image.

2. Description of Related Art

When performing ultrasonic endoscopy or laparoscope surgery, an operator performs diagnosis and surgery, assuming anatomical position under current observation, while preconceiving known anatomical relational positions of viscera or organs in a living body. To assist such diagnosis and surgery, there have been proposed techniques for displaying a guiding image for guiding a position under observation in inspection and surgery, through synthesis based on a CT image and MRI image obtained in advance.

As an example of such a medical guiding apparatus, Japanese Patent Application Laid-Open No. 10-151131 describes a medical guiding apparatus that detects the position of an ultrasonic probe, obtains from image data a tomographic image corresponding to a tomographic position of an ultrasonic image, and then displays the obtained tomographic image and the ultrasonic image in juxtaposed, superposed, or constant-interval alternate manner.

Further, Japanese Patent Application Laid-Open No. 2005-312770 describes a medical guiding apparatus that detects a distal end position of an ultrasonic endoscope, constructs a guiding image corresponding to an anatomical position of the ultrasonic endoscope based on anatomical image data, and displays the constructed image.

Still further, Japanese Patent Application Laid-Open No. 2004-113629 describes a technique that detects a position and orientation of a scanning surface of an ultrasonic probe, so as to display an accurate guiding image.

In addition, Japanese Patent Application Laid-Open No. 2002-345725 describes a medical guiding apparatus that displays a three-dimensional model image corresponding to a distal end position of an endoscope, by generating a three-dimensional viscus model image from medical image data obtained by prephotographing, further sequentially correcting the three-dimensional viscus model according to fluctuation amount of the viscus per unit time, and then detecting the position of the distal end of the endoscope.

By the way, in CT and MRI for obtaining image data in advance (prior to using a medical instrument), a subject is usually photographed in a supine position. In contrast, inspection, surgery, and so forth, using a medical instrument such as an endoscope and an ultrasonic endoscope, are performed with the subject in a left lateral or prone position. However, because the gravitational direction with respect to the body is different between the supine position and the left lateral or prone position, positional relations of viscera and blood vessels in a body cavity would be subject to change. Therefore, a guiding image produced for an image obtaining position in performing endoscopy, based on a CT or MRI image photographed with the subject in the supine position, would be different from an endoscopic or ultrasonic image obtained in endoscopy, in terms of positions of viscera in the body cavity.

The above-mentioned situation occurs not only in the above case but also when using a laparoscope or an extracorporeal ultrasonic diagnostic apparatus, if the subject is not in the supine position.

Moreover, when, for example, performing tissue sampling in narrow bronchia disallowing insertion of an endoscope, by inserting a treatment instrument or the like into a bronchial endoscope channel, it is necessary to make a distal end position of the treatment instrument reach a tissue sampling location while observing only the above-described guiding image, since endoscopic image observation can not be performed. Accordingly, in a case like this, a highly accurate guiding image is required that eliminates a deviation between actual position of the treatment instrument and position thereof in the guiding image.

SUMMARY OF THE INVENTION

An object of the present invention is to provide a medical guiding system, a medical guiding program, and a medical guiding method allowing position of a medical instrument on a guiding image to highly accurately agree with actual position of the instrument, irrespective of body position of a subject.

Simply put, one aspect of the present invention provides a medical guiding system, including: detecting means for detecting position and orientation of a medical instrument; preserving means for preserving medical image data obtained before use of the medical instrument; correcting means for correcting at least one of position and direction of at least one of a viscus and an organ, in line with body position of a subject; and calculating means for calculating position of the medical instrument in the medical image data corrected by the correcting means, based on position of the medical instrument detected by the detecting means.

Another aspect of the present invention provides a medical guiding program causing a computer to perform the steps of: detecting position and orientation of a medical instrument; preserving medical image data obtained before use of the medical instrument; correcting at least one of position and direction of at least one of a viscus and an organ, in line with a body position of a subject; and calculating position of the medical instrument in the medical image data corrected by the correcting step, based on a position of the medical instrument detected by the detecting step.

Still another aspect of the present invention provides a medical guiding method, including the steps of: detecting position and orientation of a medical instrument; preserving medical image data obtained before use of the medical instrument; correcting at least one of position and direction of at least one of a viscus and an organ, in line with a body position of a subject; and calculating a position of the medical instrument in the medical image data corrected by the correcting step, based on a position of the medical instrument detected by the detecting step.

The above and other objects, features and advantages of the invention will become more clearly understood from the following description referring to the accompanying drawings.

DETAILED DESCRIPTION OF PREFERRED EMBODIMENTS

Referring to the drawings, embodiments of the present invention are described below.

First Embodiment

Figure 1:
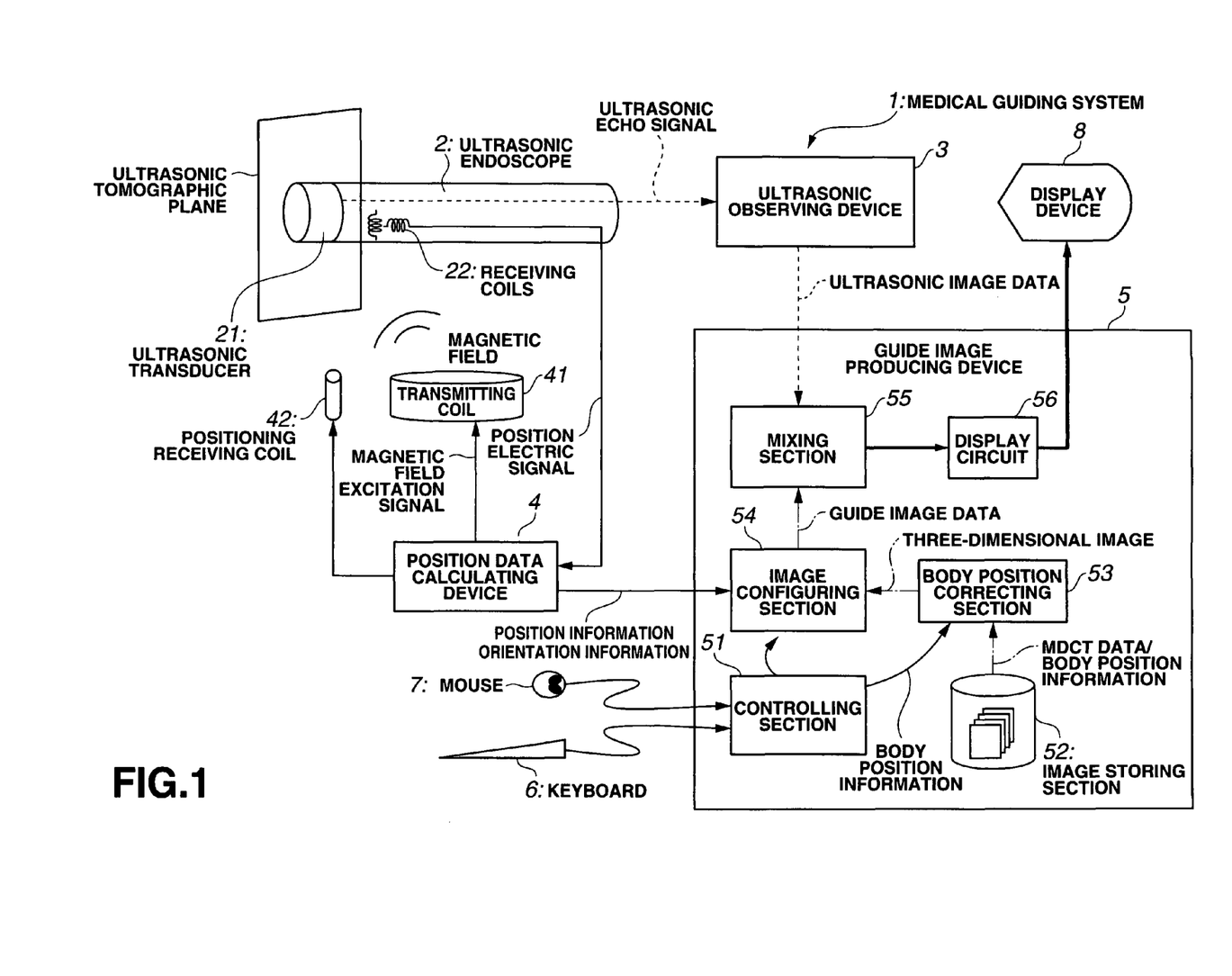
FIG. 1 is a block diagram to illustrate a configuration of a medical guiding system according to a first embodiment of the present invention.
Figure 2:
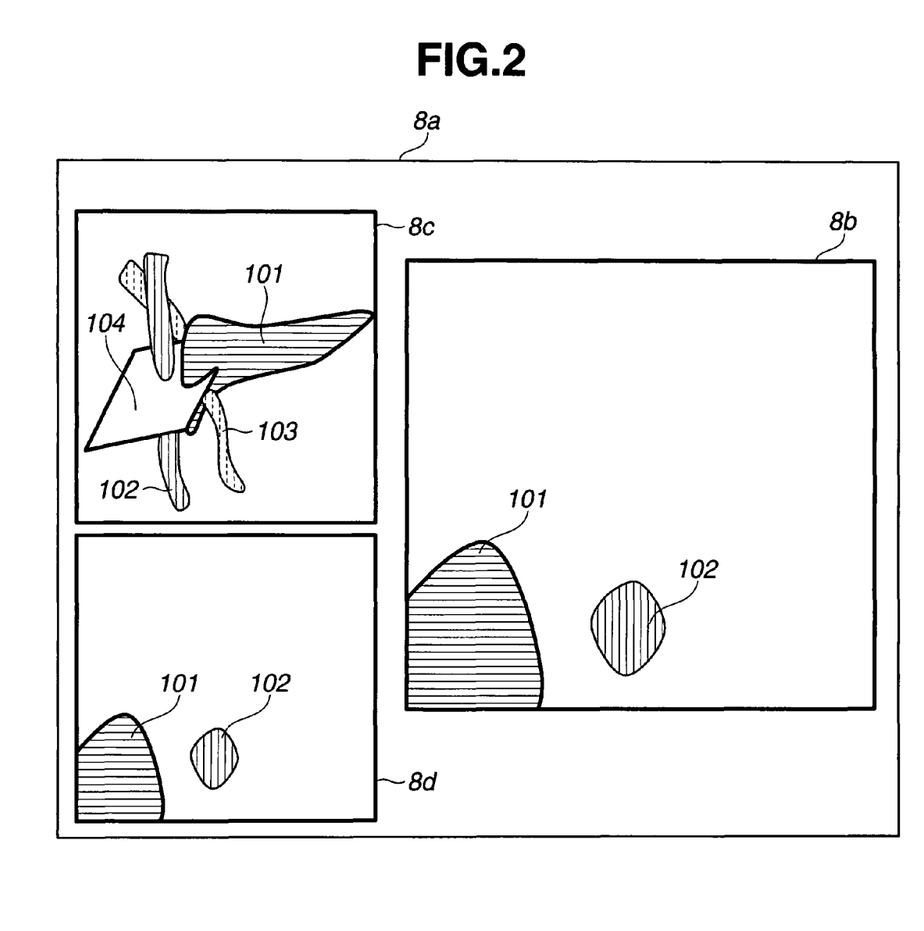
FIG. 2 is a view to illustrate a situation where three- and two-dimensional guiding images and an ultrasonic image are juxtaposed on a display screen of a display device, in the first embodiment.
Figure 3:
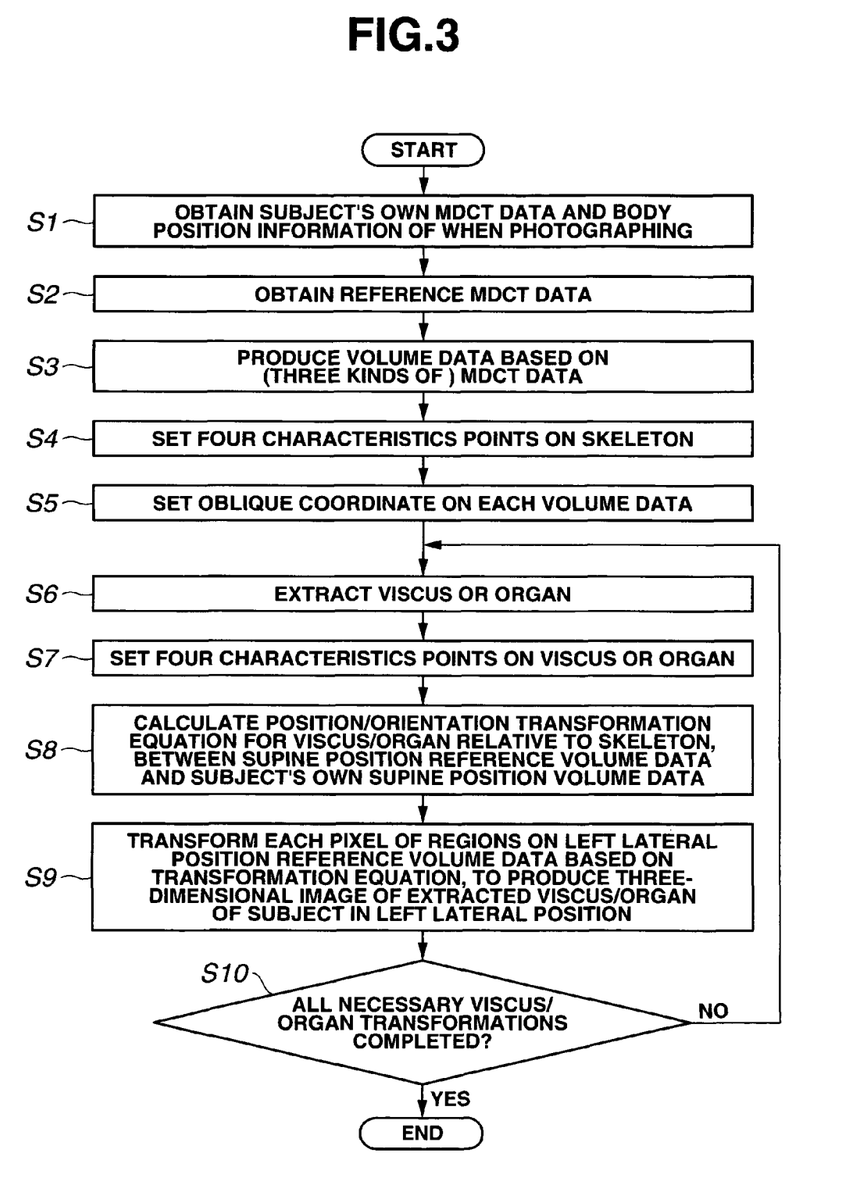
FIG. 3 is a flowchart to illustrate operations of a body position correcting section of the medical guiding system according to the first embodiment.
Figure 4A:
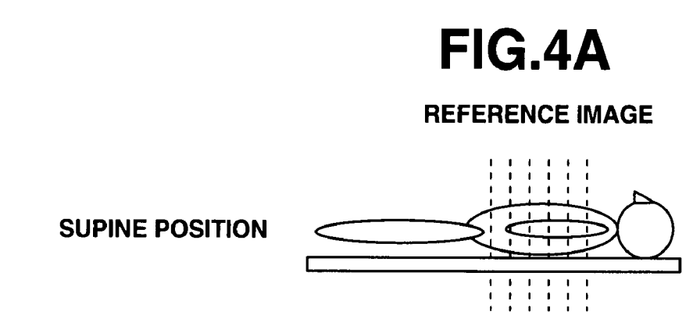
FIGS. 4A to 4D are views to illustrate overview of processings by the body position correcting section of the medical guiding system according to the first embodiment.
Figure 4B:
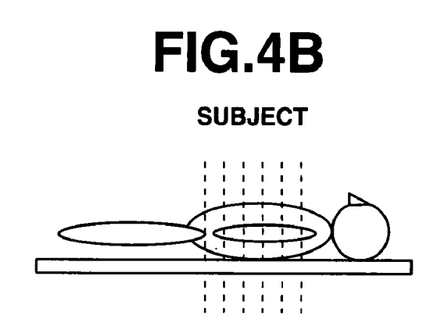
Figure 4C:
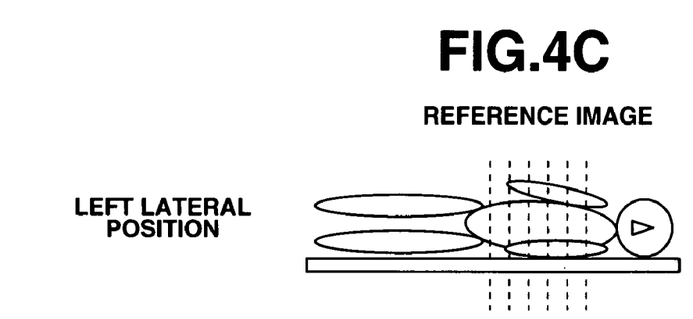
Figure 4D:
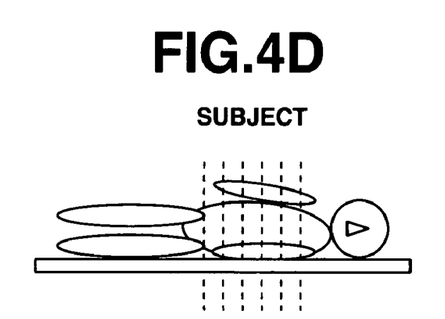
Figure 5:
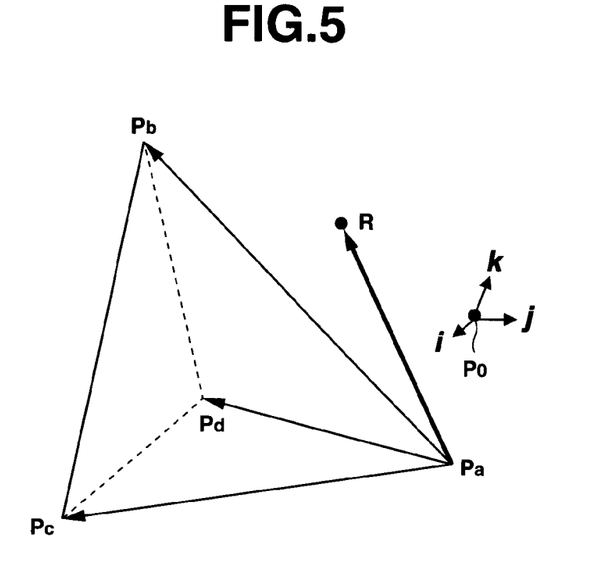
FIG. 5 is a view to illustrate an oblique coordinate system set to supine position reference volume data, in the first embodiment.
Figure 6:
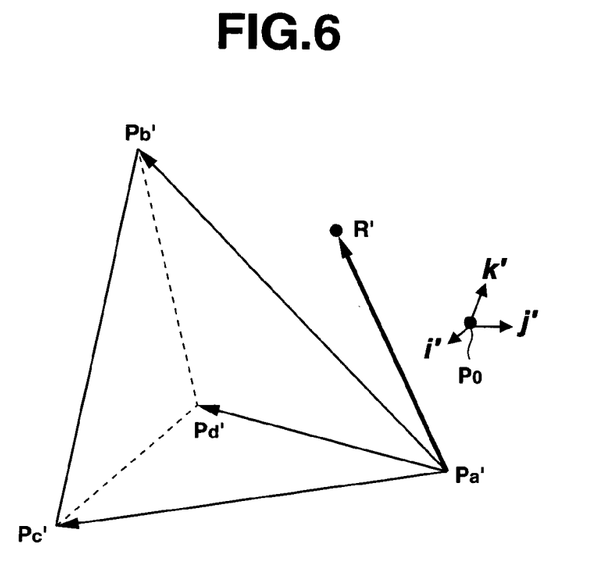
FIG. 6 is a view to illustrate an oblique coordinate system set to subject's own supine position volume data, in the first embodiment.

FIGS. 1 to 6 illustrate a first embodiment of the present invention. FIG. 1 is a block diagram to illustrate a configuration of a medical guiding system; FIG. 2 is a view to illustrate a situation where three- and two-dimensional guiding images and an ultrasonic image are juxtaposed on a display screen of a display device; FIG. 3 is a flowchart to illustrate operations of a body position correcting section of the medical guiding system; FIGS. 4A to 4D are views to illustrate overview of processings by the body position correcting section of the medical guiding system; FIG. 5 is a view to illustrate an oblique coordinate system set to supine position reference volume data; and FIG. 6 is a view to illustrate an oblique coordinate system set to subject's own supine position volume data.

The present embodiment will be described assuming that medical instrument whose position and orientation are detected by detecting means is an ultrasonic endoscope.

A medical guiding system 1 of the present embodiment includes an ultrasonic endoscope 2; an ultrasonic observing device 3; a position data calculating device 4; a guide image producing device 5; a keyboard 6; a mouse 7; and a display device 8, and serves as a system for guiding the ultrasonic endoscope 2 as a medical instrument.

The ultrasonic endoscope 2 includes an ultrasonic transducer 21 disposed at a distal end of the ultrasonic endoscope, and two receiving coils 22 serving as detecting means disposed at the rear of the ultrasonic transducer 21, in a fixed positional relation therewith. The ultrasonic transducer 21 is connected to the ultrasonic observing device 3, while the two receiving coils 22 are connected to the position data calculating device 4. The two receiving coils 22 have rolling axis directions mutually separated from each other.

The ultrasonic observing device 3 is connected to the ultrasonic transducer 21 incorporated in the ultrasonic endoscope 2 as mentioned above, as well as further to the guide image producing device 5.

The position data calculating device 4 is connected to the receiving coils 22 incorporated in the ultrasonic endoscope 2 as mentioned above, as well as further to the guide image producing device 5. The position data calculating device 4 is detecting means including a transmitting coil 41 and a positioning receiving coil 42. The transmitting coil 41 incorporates a plurality of electromagnetic field generating coils not shown, and is detecting means for generating an alternating magnetic field, as described later. The positioning receiving coil 42 is detecting means for receiving an alternating magnetic field generated by the transmitting coil 41, to perform a positioning.

The guide image producing device 5 includes a controlling section 51; an image storing section 52 serving as preserving means; a body position correcting section 53 serving as correcting means; an image configuring section 54 serving as calculating means; a mixing section 55; and a display circuit 56. The mixing section 55 is connected to the ultrasonic observing device 3; the image configuring section 54 to the position data calculating device 4; the controlling section 51 to the keyboard 6 and the mouse 7; and the display circuit 56 to the display device 8. Inside the guide image producing device 5, the body position correcting section 53 is connected to the controlling section 51, the image storing section 52, and the image configuring section 54; the image configuring section 54 to the controlling section 51, the body position correcting section 53, and the mixing section 55; and the mixing section 55 to the image configuring section 54 and the display circuit 56. Note that, although not shown, the controlling section 51 is also connected with and controls the image storing section 52, the mixing section 55, and the display circuit 56.

Next, actions of the medical guiding system 1 are described.

First, referring to FIG. 1, overview of the actions of the medical guiding system 1 is described. Note that arrow lines in FIG. 1 show signal/data flows as set forth below. That is, a solid line shows a position-related signal/data flow; a broken line shows an ultrasonic wave related signal/data flow; a bold line shows a signal/data flow related to a final display image; a dash-dotted line shows a signal/data flow related to a guide image; and a curved line shows a signal/data flow related to other controls.

An operator (hereinbelow, an operator or helper or the like is simply represented and referred to as "operator") inserts the ultrasonic endoscope 2 into a body cavity of the subject, and operates the ultrasonic observing device 3 to start an ultrasonic scan.

When the ultrasonic scan is started, the ultrasonic transducer 21 sends an ultrasonic wave to the subject, receives an ultrasonic wave reflected on the subject, and then outputs an ultrasonic echo signal of an ultrasonic tomographic plane.

The ultrasonic observing device 3 receives the ultrasonic echo signal from the ultrasonic transducer 21 of the ultrasonic endoscope 2, to produce ultrasonic image data based on the received ultrasonic echo signal. Then, the ultrasonic observing device 3 outputs the produced ultrasonic image data to the mixing section 55 of the guide image producing device 5.

Meanwhile, the position data calculating device 4 excites the transmitting coil 41 to generate an alternating magnetic field (more specifically, the position data calculating device 4 supplies magnetic field generating currents of different frequencies to the plurality of electromagnetic field generating coils provided in the transmitting coil 41, to generate magnetic fields of different frequencies). In turn, the receiving coils 22 incorporated in the endoscope detects the alternating magnetic field from the transmitting coil 41 and converts the magnetic field to a position electric signal which is outputted to the position data calculating device 4.

Upon receiving the position electric signal from the receiving coils 22, the position data calculating device 4 separates the signal for each frequency, and calculates position information and orientation information of the receiving coils 22 based on each of the separated position electric signals. The position data calculating device 4 outputs the calculated position information and orientation information to the image configuring section 54 of the guide image producing device 5.

The guide image producing device 5 performs following processings.

First, the image storing section 52 preserves therein MDCT data (subject's own medical image data) including a plurality pieces of subject's own sliced data obtained by MDCT (multidetector computed tomography), along with body position information, such as supine and left lateral positions, of when the MDCT data was photographed. Furthermore, the image storing section 52 preserves therein reference MDCT data (reference medical image data) of a different person (another subject) other than the subject, photographed in various body position such as supine, left lateral, right lateral, and prone positions, along with body position information of when the reference MDCT data was photographed. It is noted here that MDCT is CT in which a plurality of lines of detectors are provided in a body axial direction, wherein data from each of the lines of detectors arranged in the body axial direction are subject to image-calculation, thus allowing one scan to obtain sliced data of a plurality of tomographic planes.

When the operator operates the mouse 7 and the keyboard 6 to instruct a body position of the subject of when performing inspection with the ultrasonic endoscope 2, a signal based on the instruction is inputted to the controlling section 51 of the guide image producing device 5. In turn, the controlling section 51 outputs information on the body position of when performing inspection with the ultrasonic endoscope 2, to the body position correcting section 53.

Upon receiving an input of current body position information from the controlling section 51, the body position correcting section 53 obtains from the image storing section 52, the subject's own MDCT data and the body position information of the subject of when the images were photographed. The body position correcting section 53 compares the current body position information and the body position information of the subject of when the images were photographed. If the information agree to each other, the body position correcting section 53 constructs a three-dimensional image obtained by extracting a specific viscera or organs from the subject's own MDCT data, and outputs the constructed three-dimensional image to the image configuring section 54. On the other hand, if the current body position information and the body position information of the subject of when the images were photographed do not agree to each other, the body position correcting section 53 calculates, to a transformation equation, a personal difference in position and direction for each viscus or organ, based on the subject's own MDCT data and the reference MDCT data obtained in the same body position as that of when the MDCT data was obtained, and then applies the transformation equation to reference MDCT data obtained in the same body position as that of the subject of when performing inspection with the ultrasonic endoscope 2, to produce a three-dimensional image of the extracted specific viscera or organs of the subject of when performing the endoscopy, as will be detailed later. The three-dimensional image thus produced by the body position correcting section 53 is outputted to the image configuring section 54.

Next is described a method for positioning the ultrasonic image data and the three-dimensional image of the extracted specific viscera or organs.

When the operator instructs the controlling section 51 of the guide image producing device 5 to start the positioning, by operating the mouse 7 and the keyboard 6, the controlling section 51 outputs positioning start information to the image configuring section 54.

On receiving the positioning starting information, then based on the three-dimensional image of the extracted specific viscera or organs inputted from the body position correcting section 53, the image configuring section 54 produces two-dimensional image data for specifying characteristics point thereon, obtained by slicing the three-dimensional image in a plane orthogonal to the body axial direction. The image configuring section 54 then outputs the produced two-dimensional image data for specifying characteristics point to the mixing section 55.

The mixing section 55 produces digital data for display, juxtaposing the ultrasonic image data from the ultrasonic observing device 3 and the two-dimensional image data for specifying characteristics point from the image configuring section 54, and then outputs the produced digital data to the display circuit 56.

The display circuit 56 converts the digital data inputted from the mixing section 55 to an output signal for display, which is outputted to the display device 8.

The display device 8, which displays an image based on an output signal from the display circuit 56, displays the two-dimensional image data for specifying characteristics point and the ultrasonic image data.

The operator selects an anatomical characteristics point on the two-dimensional image data for specifying characteristics point, while varying position of the two-dimensional image data for specifying characteristics point in the body axial direction by operating the keyboard 6 and the mouse 7.

Upon receiving the selection by the operator via the controlling section 51, the image configuring section 54 calculates the position of the characteristics point on the three-dimensional image of the extracted specific viscera or organs.

Thereafter, the operator brings the positioning receiving coil 42 or the ultrasonic endoscope 2 into contact with an anatomical characteristics point of the subject identical with the anatomical characteristics point selected using the keyboard 6 and the mouse 7, and then instructs to obtain position data by operating the keyboard 6 and the mouse 7. In response, the controlling section 51 outputs a position data obtaining instruction to the image configuring section 54. Upon receiving the position data obtaining instruction from the controlling section 51, the image configuring section 54 associates the position data inputted from the position data calculating device 4 with the characteristics point on the three-dimensional image of the extracted specific viscera or organs.

By performing the association between the characteristics point and the position data with respect to a plurality of characteristics points, the positioning between the ultrasonic image data and the three-dimensional image of the extracted specific viscera or organs completes.

After the positioning completes, when the operator instructs the controlling section 51 of the guide image producing device 5 to start guiding of the subject by operating the mouse 7 and the keyboard 6, the controlling section 51 outputs a guide starting instruction to the image configuring section 54.

Upon receiving the guide starting instruction from the controlling section 51, the image configuring section 54 calculates a position where the ultrasonic image data of the ultrasonic endoscope 2 was obtained, based on the three-dimensional image of the extracted specific viscera or organs inputted from the body position correcting section 53, and the position information and orientation information of the receiving coils 22 of the ultrasonic endoscope 2 inputted from the position data calculating device 4. Further, based on a result of the above-mentioned positioning, the image configuring section 54 calculates a position where the ultrasonic image data was obtained, in the three-dimensional image of the extracted specific viscera or organs, to produce guide image data.

Here, as shown in FIG. 2, the guide image data includes data of a three-dimensional guide image 8c (three-dimensional guide image data) and data of a two-dimensional guide image 8d (two-dimensional guide image data).

The three-dimensional guide image data is image data wherein an ultrasonic tomographic plane marker 104 representing the ultrasonic image data obtaining position is superposed on the three-dimensional image of the extracted specific viscera or organs (a pancreas 101, a main artery 102, and a portal system blood vessel 103 in the example shown in FIG. 2) inputted from the body position correcting section 53.

The two-dimensional guide image data is image data of a cross section (two-dimensional plane) agreeing with the ultrasonic image data in anatomical position and orientation, cut out from the three-dimensional image of the extracted specific viscera or organs.

As a specific example, a case is taken where the ultrasonic image data (see an ultrasonic image 8b in the display screen 8a of the display device 8) is image data of a cross section of a head portion of the pancreas (see the pancreas 101 in FIG. 2) as viewed from a duodenum, as shown in FIG. 2. In this case, the image configuring section 54 produces three-dimensional guide image data in which the ultrasonic tomographic plane marker 104 is displayed at the duodenum and the head portion of the pancreas in the three-dimensional image, based on the three-dimensional image of the extracted specific viscera or organs. The image configuring section 54 further produces two-dimensional guide image data of a cross section of the head portion of the pancreas as viewed from the duodenum, cut out from the three-dimensional image. The image configuring section 54 then outputs the produced guide image data to the mixing section 55.

The mixing section 55 produces digital data for display, juxtaposing the ultrasonic image data from the ultrasonic observing device 3 and the two kinds of guide image data from the image configuring section 54.

The display circuit 56 converts the digital data from the mixing section 55 to an output signal for display.

Based on the output signal from the display circuit 56, the display device 8 displays, juxtaposing, the ultrasonic image 8b and the guide images (the three-dimensional guide image 8c and the two-dimensional guide image 8d) on the display screen 8a, as shown in FIG. 2.

In this manner, the operator can perform accurate diagnosis, viewing the guide images 8c, 8d displayed on the display screen 8a of the display device 8 to recognize which anatomical part of the subject the position currently observed on the ultrasonic image 8b is.

Next, referring to a flowchart of FIG. 3, actions of the body position correcting section 53 according to an actual use example thereof are described in detail.

Note that, in describing the flowchart, it is assumed that the MDCT data as reference images preserved in the image storing section 52 includes those obtained in the supine position as shown in FIG. 4A and those obtained in the left lateral position as shown in FIG. 4C. Furthermore, it is assumed that the subject's own MDCT data preserved in the image storing section 52 is one obtained in the supine position as shown in FIG. 4B, and that the body position of the subject when performing inspection with the ultrasonic endoscope 2 is the left lateral position as shown in FIG. 4D. Therefore, in this example, the three-dimensional image of the subject's own extracted specific viscera or organs produced by the body position correcting section 53 is a three-dimensional image in the left lateral position.

Outline of the actions of the body position correcting section 53 to be detailed below is described as follows. First, the body position correcting section 53 calculates, to a transformation equation, a personal difference in position and direction for each viscus or organ, based on supine position reference MDCT data as shown in FIG. 4A and subject's own supine position MDCT data as shown in FIG. 4B. Next, the body position correcting section 53 applies the calculated equation to left lateral position reference MDCT data as shown in FIG. 4C, thereby producing a three-dimensional image of extracted specific viscera or organs of the subject himself/herself in the left lateral position. In this manner, operations of the body position correcting section 53 are performed.

Upon receiving from the controlling section 51 an input of "left lateral position" which is body position information of when performing inspection with the ultrasonic endoscope 2, the body position correcting section 53 reads out the subject's own MDCT data obtained in the supine position (see FIG. 4B) and "supine position" which is body position information of when this MDCT data was photographed, preserved in the image storing section 52 (step S1).

Next, the body position correcting section 53 reads out from the reference MDCT data preserved in the image storing section 52, obtained by photographing a different person other than the subject in various body positions, the left lateral position reference MDCT data (see FIG. 4C) obtained in a body position corresponding to the "left lateral position" that is the body position information of when performing inspection with the ultrasonic endoscope 2, obtained in step S1; and the supine position reference MDCT data (see FIG. 4A) obtained in a body position corresponding to the "supine position" that is the body position information of when the subject's own MDCT data was photographed (step S2).

Subsequently, the body position correcting section 53 renders the subject's own supine position MDCT data obtained in step S1, and the supine position reference MDCT data and the left lateral position reference MDCT data read out in step S2, to pieces of volume data, respectively, to produce subject's own supine position volume data, supine position reference volume data, and left lateral position reference volume data (step S3).

Furthermore, the body position correcting section 53 sets four characteristics points on a skeleton in each of the volume data by operator input or automatic calculation. In the present embodiment, it is assumed that the four characteristics points to be set on the skeleton are a xiphisternum, a right edge of pelvis, a left edge of pelvis, and an on-spine point on a line connecting the right and left pelvis edges. Note that the four characteristics points on each volume data are attached with reference symbols as follows. Provided on the supine position reference volume data are a xiphisternum $P_0$, a right edge of pelvis $P_1$, a left edge of pelvis $P_2$, and an on-spine point $P_3$ connecting the right and left pelvis edges. Provided on the subject's own supine position volume data are a xiphisternum $P_0'$, a right edge of pelvis $P_1'$, a left edge of pelvis $P_2'$, and an on-spine point $P_3'$ connecting the right and left pelvis edges.

Provided on the left lateral position reference volume data are a xiphisternum $P_0''$, a right edge of pelvis $P_1''$, a left edge of pelvis $P_2''$, and an on-spine point $P_3''$ connecting the right and left pelvis edges (step S4).

Then, the body position correcting section 53 sets the xiphisterna $P_0$, $P_0'$, $P_0''$, each being one of the four characteristics points on the each volume data, as the origins of the volume data, and introduces an oblique coordinate on each of the volume data using vectors from the origin to the remaining three points, that is: vectors i, j, k on the supine position reference volume data; vectors i', j', k' on the subject's own supine position volume data; and vectors i", j", k" on the left lateral position reference volume data (for notational reason, hereinbelow in the present specification, vectors and matrices will be denoted in normal characters, instead of using bold letters or attaching an arrow on top thereof), as shown in Eq. 1 below (step S5). In the following calculations, these oblique coordinates are used.

$$i = \overrightarrow{P_0P_1}, \; j = \overrightarrow{P_0P_2}, \; k = \overrightarrow{P_0P_3} \quad \text{[Eq. 1]}$$
$$i' = \overrightarrow{P_0'P_1'}, \; j' = \overrightarrow{P_0'P_2'}, \; k' = \overrightarrow{P_0'P_3'}$$
$$i'' = \overrightarrow{P_0''P_1''}, \; j'' = \overrightarrow{P_0''P_2''}, \; k'' = \overrightarrow{P_0''P_3''}$$

Processings in the subsequent steps S6 to S9 are performed for each region (viscus or organ) displayed in a guide image. Therefore, to display a plurality of regions in the guide image, it is necessary to repeatedly perform the processings in steps S6 to S9, a plurality of times.

In the present embodiment, it is assumed that regions to be used for the guiding are a main blood vessel in the artery system, a main blood vessel in the portal system, a pancreas, a gallbladder, a liver, a lien, and a kidney. Note that, although only the blood vessel in the artery system will be described hereinbelow for descriptive convenience, the processings in steps S6 to S9 are to be similarly repeatedly performed for other viscera or organs.

In other words, the body position correcting section 53 extracts a main blood vessel in the artery system for each of the supine position reference volume data, the subject's own supine position volume data, and the left lateral position reference volume data (step S6).

Next, the body position correcting section 53 specifies four characteristics points such as a blood vessel branch point, on the regions extracted in step S6 by operator specification or automatic calculation (step S7). Here, the characteristics points specified on the supine position reference volume data are denoted as $P_a$, $P_b$, $P_c$, and $P_d$, respectively. The characteristics points specified on the subject's own supine position volume data are denoted as $P_a'$, $P_b'$, $P_c'$, and $P_d'$, respectively. Of these characteristics points, $P_a$ and $P_a'$, $P_b$ and $P_b'$, $P_c$ and $P_c'$, and $P_d$ and $P_d'$ respectively represent anatomically the same positions.

In the oblique coordinate systems $P_0$-ijk and $P_0'$-i'j'k' set on respective volume data in step S5, positions of those characteristics points on the oblique coordinates can be represented as shown in the following Eqs. 2 and 3.

$$\overrightarrow{P_0P_a} = a_1 i + a_2 j + a_3 k \quad \text{[Eq. 2]}$$
$$\overrightarrow{P_0P_b} = b_1 i + b_2 j + b_3 k$$

-continued
$$\overrightarrow{P_0P_c} = c_1 i + c_2 j + c_3 k$$
$$\overrightarrow{P_0P_d} = d_1 i + d_2 j + d_3 k$$

$$\overrightarrow{P_0'P_a'} = a_1' i' + a_2' j' + a_3' k' \quad \text{[Eq. 3]}$$
$$\overrightarrow{P_0'P_b'} = b_1' i' + b_2' j' + b_3' k'$$
$$\overrightarrow{P_0'P_c'} = c_1' i' + c_2' j' + c_3' k'$$
$$\overrightarrow{P_0'P_d'} = d_1' i' + d_2' j' + d_3' k'$$

By the way, it is considered that location and size of each viscus relative to skeleton of a human body are different from person to person. Accordingly, based on the four points specified in step S7, a transformation equation is calculated to transform position and direction of the main blood vessel in the artery system on the supine position reference volume data to position and direction of the main blood vessel in the artery system on the subject's own supine position volume data, to formulate personal difference in viscus position (step S8).

Referring to FIGS. 5 and 6, means for the formulating in step S8 is described below.

Supposing that a random point R on the main blood vessel in the artery system on the supine position reference volume data is at a specific position with respect to a triangular pyramid $P_aP_bP_cP_d$ shown in FIG. 5, it can be assumed that a point R' at an equivalent position with respect to a triangular pyramid $P_a'P_b'P_c'P_d'$ shown in FIG. 6 on the subject's own supine position volume data corresponds to the same point as the point R on the main blood vessel in the artery system. Under this assumption, the following Eqs. 4 and 5 using proper real numbers a, b and c hold.

$$\overrightarrow{P_aR} = a\overrightarrow{P_aP_b} + b\overrightarrow{P_aP_c} + c\overrightarrow{P_aP_d} \quad \text{[Eq. 4]}$$

$$\overrightarrow{P_a'R'} = a\overrightarrow{P_a'P_b'} + b\overrightarrow{P_a'P_c'} + c\overrightarrow{P_a'P_d'} \quad \text{[Eq. 5]}$$

Here, if directional components of a position vector $P_aR$ of the point R in oblique coordinate axes i, j, k are defined as $x_R$, $y_R$, $z_R$, respectively, then the following Eq. 6 holds.

$$\overrightarrow{P_0R} = x_R i + y_R j + z_R k \quad \text{[Eq. 6]}$$

Similarly, if directional components of a position vector $P_a'R'$ of the point R' in oblique coordinate axes i', j', k' are defined as $x_R'$, $y_R'$, $z_R'$, respectively, then the following Eq. 7 holds.

$$\overrightarrow{P_0'R'} = x_R' i' + y_R' j' + z_R' k' \quad \text{[Eq. 7]}$$

In the following, based on the above-described equations, position vector $\overrightarrow{P_0'R'}$ of the corresponding point R' on the subject's own supine position volume data, and directional components $x_R'$, $y_R'$, $z_R'$ of the corresponding point R' in the oblique coordinate will be determined from the random point R on the supine position reference volume data.

First, expressing the Eq. 4 as a position vector from the origin $P_0$ results in the following Eq. 8.

$$\overrightarrow{P_0R} - \overrightarrow{P_0P_a} = \quad [\text{Eq. 8}]$$
$$a(\overrightarrow{P_0P_b} - \overrightarrow{P_0P_a}) + b(\overrightarrow{P_0P_c} - \overrightarrow{P_0P_a}) + c(\overrightarrow{P_0P_d} - \overrightarrow{P_0P_a})$$

Expressing the components of the Eq. 8 using the Eqs. 2 and 6 results in the following Eq. 9.

$$\begin{pmatrix} x_R \\ y_R \\ z_R \end{pmatrix} - \begin{pmatrix} a_1 \\ a_2 \\ a_3 \end{pmatrix} = \begin{pmatrix} b_1 - a_1 & c_1 - a_1 & d_1 - a_1 \\ b_2 - a_2 & c_2 - a_2 & d_2 - a_2 \\ b_3 - a_3 & c_3 - a_3 & d_3 - a_3 \end{pmatrix} \begin{pmatrix} a \\ b \\ c \end{pmatrix} \quad [\text{Eq. 9}]$$

Here, to simply express the following equations, there is defined a 3 by 3 matrix Q as shown in the following Eq. 10.

$$Q = \begin{pmatrix} b_1 - a_1 & c_1 - a_1 & d_1 - a_1 \\ b_2 - a_2 & c_2 - a_2 & d_2 - a_2 \\ b_3 - a_3 & c_3 - a_3 & d_3 - a_3 \end{pmatrix} \quad [\text{Eq. 10}]$$

Substitution of the Eq. 10 to the Eq. 9 results in the following Eq. 11.

$$\begin{pmatrix} x_R \\ y_R \\ z_R \end{pmatrix} - \begin{pmatrix} a_1 \\ a_2 \\ a_3 \end{pmatrix} = Q \begin{pmatrix} a \\ b \\ c \end{pmatrix} \quad [\text{Eq. 11}]$$

Thus, multiplying an inverse matrix of the matrix Q on both sides of the Eq. 11 from the left results in the following Eq. 12.

$$\begin{pmatrix} a \\ b \\ c \end{pmatrix} = Q^{-1} \left\{ \begin{pmatrix} x_R \\ y_R \\ z_R \end{pmatrix} - \begin{pmatrix} a_1 \\ a_2 \\ a_3 \end{pmatrix} \right\} \quad [\text{Eq. 12}]$$

Meanwhile, expressing the Eq. 5 as a position vector from the origin $P_0'$ results in the following Eq. 13, as the Eq. 4 resulted in the Eq. 8.

$$\overrightarrow{P_0'R'} - \overrightarrow{P_0'P_a'} = \quad [\text{Eq. 13}]$$
$$a(\overrightarrow{P_0'P_b'} - \overrightarrow{P_0'P_a'}) + b(\overrightarrow{P_0'P_c'} - \overrightarrow{P_0'P_a'}) + c(\overrightarrow{P_0'P_d'} - \overrightarrow{P_0'P_a'})$$

Furthermore, expressing the components of the Eq. 13 using the Eqs. 3 and 7 results in the following Eq. 14, as applying the Eqs. 2 and 6 to the Eq. 8 resulted in the Eq. 9.

$$\begin{pmatrix} x_R' \\ y_R' \\ z_R' \end{pmatrix} - \begin{pmatrix} a_1' \\ a_2' \\ a_3' \end{pmatrix} = \begin{pmatrix} b_1' - a_1' & c_1' - a_1' & d_1' - a_1' \\ b_2' - a_2' & c_2' - a_2' & d_2' - a_2' \\ b_3' - a_3' & c_3' - a_3' & d_3' - a_3' \end{pmatrix} \begin{pmatrix} a \\ b \\ c \end{pmatrix} \quad [\text{Eq. 14}]$$

Here also, to simply express the following equations, there is defined a 3 by 3 matrix Q' as shown in the following Eq. 15.

$$Q' = \begin{pmatrix} b_1' - a_1' & c_1' - a_1' & d_1' - a_1' \\ b_2' - a_2' & c_2' - a_2' & d_2' - a_2' \\ b_3' - a_3' & c_3' - a_3' & d_3' - a_3' \end{pmatrix} \quad [\text{Eq. 15}]$$

Substitution of the Eq. 15 to the Eq. 14 results in the following Eq. 16.

$$\begin{pmatrix} x_R' \\ y_R' \\ z_R' \end{pmatrix} - \begin{pmatrix} a_1' \\ a_2' \\ a_3' \end{pmatrix} = Q' \begin{pmatrix} a \\ b \\ c \end{pmatrix} \quad [\text{Eq. 16}]$$

Because a, b and c in the right side of the Eq. 16 are defined by the above-described Eq. 12, substitution of the Eq. 12 to the Eq. 16 results in the following Eq. 17.

$$\begin{pmatrix} x_R' \\ y_R' \\ z_R' \end{pmatrix} - \begin{pmatrix} a_1' \\ a_2' \\ a_3' \end{pmatrix} = Q'Q^{-1} \left\{ \begin{pmatrix} x_R \\ y_R \\ z_R \end{pmatrix} - \begin{pmatrix} a_1 \\ a_2 \\ a_3 \end{pmatrix} \right\} \quad [\text{Eq. 17}]$$

Therefore, the following Eq. 18 is obtained.

$$\begin{pmatrix} x_R' \\ y_R' \\ z_R' \end{pmatrix} = \begin{pmatrix} a_1' \\ a_2' \\ a_3' \end{pmatrix} + Q'Q^{-1} \left\{ \begin{pmatrix} x_R \\ y_R \\ z_R \end{pmatrix} - \begin{pmatrix} a_1 \\ a_2 \\ a_3 \end{pmatrix} \right\} \quad [\text{Eq. 18}]$$

Thus, using the Eqs. 7 and 18, the position vector $\overrightarrow{P_0'R'}$ of the corresponding point R' on the subject's own supine position volume data, and the directional components $x_R'$, $y_R'$, $z_R'$ of the corresponding point R' in the oblique coordinate were determined from the random point R on the supine position reference volume data.

Thus was formulated the relation between the main blood vessel in the artery system on the supine position reference volume data and the main blood vessel in the artery system on the subject's own supine position volume data.

When the above-described processing of step S8 ends, processing in step S9 is performed next. That is, based on the relation equation (personal difference in viscus position) between the main blood vessel in the artery system on the supine position reference volume data and the main blood vessel in the artery system on the subject's own supine position volume data, calculated in the above-described step S8, position of the main blood vessel in the artery system on the left lateral position reference volume data is corrected to an estimated position of the main blood vessel in the artery system of when the subject is brought into the left lateral position, thus producing subject's own left lateral position volume data (step S9).

Details of the processing in step S9 is described below.

First, an oblique coordinate system $P_0''\text{-}i''j''k''$ on the left lateral position reference volume data calculated in step S5 is used to express position of a pixel R" on the main blood vessel in the artery system on the left lateral position reference volume data extracted in step S6, as shown in the following Eq. 19.

$$\overrightarrow{P_0'' R''} = x_R'' i'' + y_R'' j'' + z_R'' k'' \qquad [\text{Eq. 19}]$$

Also, an oblique coordinate system $P_0''\text{-}i''j''k''$ is used to express a position R'", obtained by correcting the position of pixel R" to that of when the subject is brought into the left lateral position, as shown in the following Eq. 20.

$$\overrightarrow{P_0'' R'''} = x_R''' i'' + y_R''' j'' + z_R''' k'' \qquad [\text{Eq. 20}]$$

Then, the above-described Eq. 18 is replaced as shown in the following Eq. 21.

$$\begin{pmatrix} x_R''' \\ y_R''' \\ z_R''' \end{pmatrix} = \begin{pmatrix} a_1' \\ a_2' \\ a_3' \end{pmatrix} + Q'Q^{-1}\left\{ \begin{pmatrix} x_R'' \\ y_R'' \\ z_R'' \end{pmatrix} - \begin{pmatrix} a_1 \\ a_2 \\ a_3 \end{pmatrix} \right\} \qquad [\text{Eq. 21}]$$

Next, substitution of $x_R''$, $y_R''$, $z_R''$ in the Eq. 21 can calculate positions $x_R'''$, $y_R'''$, $z_R'''$ of the pixel R" of when the subject is brought into the left lateral position To the thus calculated positions $x_R'''$, $y_R'''$, $z_R'''$, pixel value of R" is alloted.

Performing these processings to all pixels configuring an image of the main blood vessel in the artery system completes a subject's own left lateral position three-dimensional image of the main blood vessel in the artery system.

Thereafter, it is determined whether or not the processings of steps S6 to S9 are completed for all regions desired to be displayed on the guide image (step S10). In the present embodiment, it is assumed that regions to be used for the guiding are the main blood vessel in the artery system, the main blood vessel in the portal system, the pancreas, the gallbladder, the liver, the lien, and the kidney, as mentioned above. Therefore, if this step S10 determines that the processings are not complete for all the regions, then the procedure returns to step S6 to repeatedly perform the above-described processings of steps S6 to S9 to any unprocessed region of the above-mentioned seven kinds of viscera or organs, changing the regions.

Thus, if step S10 determines that the processings are complete for all the regions, then is complete the three-dimensional image extracted specific viscera or organs of the subject himself/herself in the left lateral position, which ends this processing.

According to such first embodiment, even if the subject's body position of when performing an inspection with the ultrasonic endoscope 2 is different from the subject's body position of when the MDCT data was picked up, positions and directions of viscera or organs on the guide image can be changed in line with the subject's body position. This allows the positional relation between an ultrasonic scanning surface and peripheral viscera or organs on the guide image to accurately agree with the actual positional relation between the ultrasonic endoscope 2 and viscera or organs, which leads to quick approach to a region of interest such as a diseased part, contributing to shorten inspection time.

Moreover, because positions and directions of the viscera or organs in the MDCT data photographed in the supine position can also be corrected to those in the left lateral position, the need is eliminated to pick up MDCT data in the left lateral position for guiding in the inspection with the ultrasonic endoscope 2. In other words, a normally photographed CT image of the supine position can be used to produce a guide image for inspection with the ultrasonic endoscope 2, which permits reducing preparation burden on the subject and the operator.

In addition, in some cases in inspection with the ultrasonic endoscope 2, the ultrasonic transducer 21 is put in water accumulated in the tube cavity to obtain an ultrasonic image, because ultrasonic wave attenuates in air. At this time, the subject's body position is in some cases changed during inspection to facilitate accumulating the water in the tube cavity. Even in such a case, viscera positions in a guide image can be advantageously corrected in line with the body position during inspection, by inputting body position information.

Furthermore, positions of viscera or organs are corrected based on a body position in a divided manner for each region thus allowing optimum correction for each viscus or organ, even if personal difference in location and size exists for each viscus or organ. In this manner, the accurate agreement is rendered possible between the positional relation between the ultrasonic scanning surface and peripheral viscera or organs on the guide image, and the actual positional relation between the ultrasonic endoscope 2 and viscera or organs.

In addition, even in the case that viscera or organs are subject to change in shape for reasons such as being positioned at a lower side of the body when the subject's body position is changed, size and location of the viscera or organs are corrected with the personal differences taken into consideration, on the basis of viscera of organs on a reference CT image of a different person picked up in the same body position as the body position of when performing inspection with the ultrasonic endoscope 2, thereby allowing reproducing viscera or organs on the guide image, reflecting the shape of viscera or organs in the body position. This provides accurate agreement between the shape of viscera or organs on the actual ultrasonic image and the shape of viscera or organs on the guide image.

Even in positioning between an ultrasonic image and an anatomical three-dimensional image, two-dimensional tomographic image data can be produced from a body-position-corrected anatomical three-dimensional image, to allow specifying characteristics points on the produced two-dimensional tomographic image data. This enables the positional relation between an ultrasonic scanning surface and peripheral viscera or organs on the guide image to accurately agree with the actual positional relation between the ultrasonic endoscope 2 and viscera or organs.

Note that, although in the aforementioned, subject's own MDCT data is taken as a piece of information (subject's own medical image data) to be recorded in the image storing section 52, no limitation is placed thereon. That is, any anatomical image information of the subject himself/herself, allowing production of volume data based on the image information, such as an MRI or ultrasonic image, may be employed.

Likewise, although reference MDCT data of a person different from the subject photographed in various body positions is taken as a piece of information (reference medical image data) to be recorded in the image storing section 52, no limitation is placed thereon. That is, any image information allowing production of volume data may be employed, whether it be an MRI or ultrasonic image, or information such as a viscus model produced from a mean value of data of a plurality of persons (group of other subjects).

Also, although in the aforementioned, the medical instrument to be guided is the ultrasonic endoscope 2, no limitation is placed thereon. The medical instrument may be, for example, a laparoscope, a treatment instrument used for the laparoscope, or a treatment instrument to be inserted in a treatment instrument channel provided as a duct in an insertion portion of the endoscope.

Furthermore, although in the aforementioned, in correcting position of each viscus or organ, the transformation equation is calculated using the oblique coordinates obtained from the four points respectively set on the target viscera in the two kinds of volume data, calculation means is not limited thereto. For example, the transformation equation may be calculated using a pseudo inverse matrix, based on two sets of multiple point groups respectively specified on the viscera in the two kinds of volume data.

Second Embodiment

Figure 7:
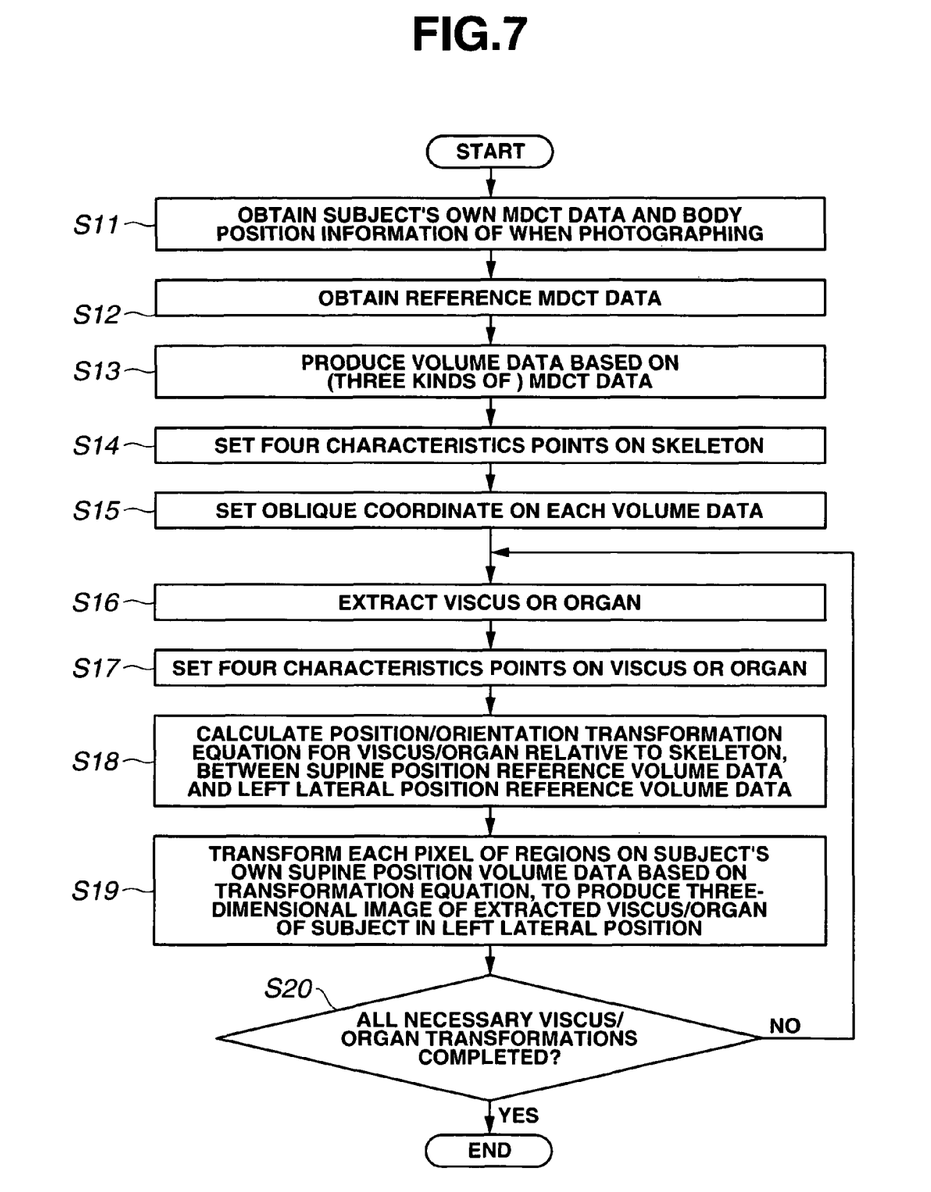
FIG. 7 is a flowchart to illustrate operations of a body position correcting section of a medical guiding system according to a second embodiment of the present invention.

FIG. 7 and FIGS. 8A to 8D show a second embodiment of the present invention. FIG. 7 is a flowchart to illustrate operations of the body position correcting section of the medical guiding system; and FIGS. 8A to 8D are views to illustrate overview of processings by the body position correcting section of the medical guiding system.

In the second embodiment, the same parts as those in the above-described first embodiment are attached with the same reference symbols, omitting descriptions thereof; only different regions will be described.

Firstly, the medical guiding system of the present embodiment has a configuration similar to that shown in FIG. 1 of the first embodiment.

However, in the medical guiding system of the present embodiment, the body position correcting section 53 of the guide image producing device 5 acts differently from that in the above-described first embodiment.

Hereinbelow, referring to the flowchart of FIG. 7, actions of the body position correcting section 53 in line with an actual use example are described in detail.

Figure 8A:
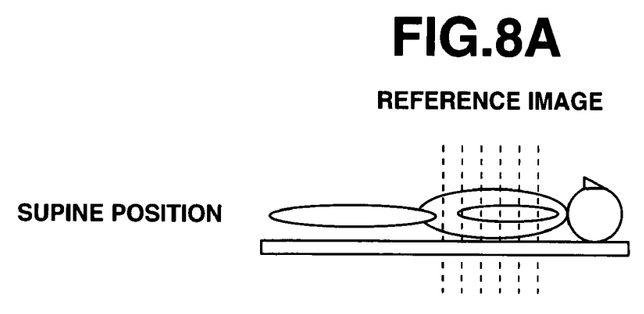
FIGS. 8A to 8D are views to illustrate overview of processings by the body position correcting section of the medical guiding system according to the second embodiment.
Figure 8B:
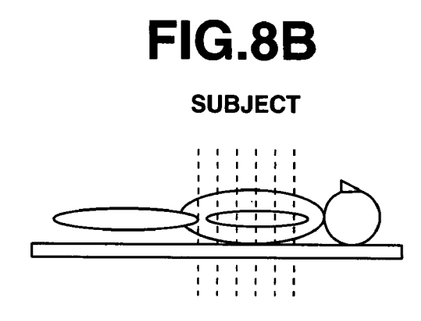
Figure 8C:
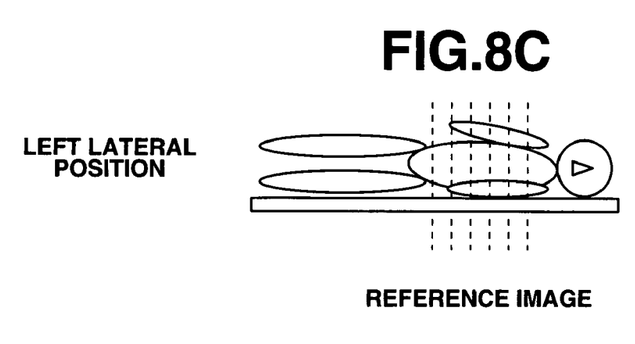
Figure 8D:
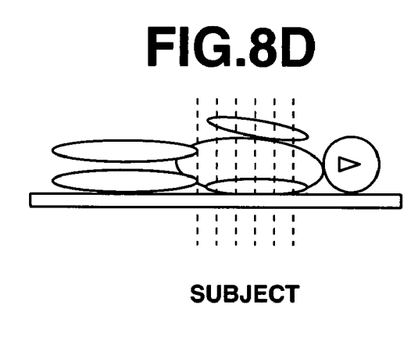

Note that, in the description of the flowchart, like in the above-described first embodiment, it is assumed that the MDCT data as reference images preserved in the image storing section 52 includes that obtained from a different person (another subject) other than the subject in the supine position as shown in FIG. 8A, and that obtained from a different person other than the subject in the left lateral position as shown in FIG. 8C. It is further assumed that the subject's own MDCT data preserved in the image storing section 52 is one obtained in the supine position as shown in FIG. 8B, and that the body position of the subject when inspected with the ultrasonic endoscope 2 is the left lateral position as shown in FIG. 8D. Therefore, also in the present embodiment will be described an exemplary case of producing a three-dimensional image of the extracted specific viscera or organs of the subject himself/herself in the left lateral position.

Overview of actions of the body position correcting section 53 to be detailed below is as follows. First, the body position correcting section 53 calculates a displacement due to body position difference for each viscus or organ to a transformation equation, based on supine position reference MDCT data as shown in FIG. 8A, and left lateral position reference MDCT data as shown in FIG. 8C. Next, the body position correcting section 53 applies the calculated transformation equation to subject's own supine position MDCT data as shown in FIG. 8B, so as to produce a three-dimensional image of extracted specific viscera or organs of the subject himself/herself in the left lateral position as shown in FIG. 8D. In this manner, operations of the body position correcting section 53 are performed.

When the processings shown in FIG. 7 start, the body position correcting section 53 performs processings shown in steps S11 to S16. These processings are respectively the same as the steps S1 to S6 in the above-described first embodiment, and therefore descriptions thereof are omitted.

Note that the processings of step S16 and of step S17 to S19 to be described next are performed for each region (viscus or organ) to be used for guiding. Thus, when a plurality of regions are desired to be used for the guiding, the processings of step S17 to S19 are repeatedly performed a plurality of times.

In the present embodiment, it is assumed that regions to be used for the guiding are the main blood vessel in the artery system, the main blood vessel in the portal system, the pancreas, the gallbladder, the liver, the lien, and the kidney. Although only the blood vessel in the artery system will be described below for descriptive simplicity, the processings of steps S16 to S19 may also be repeatedly performed for other viscera or organs as well.

That is, the body position correcting section 53 sets four characteristics points on each region extracted by the processing of step S16 by operator input or automatic calculation (step S17). Here, the characteristics points specified on the supine position reference volume data are denoted as $P_a$, $P_b$, $P_c$ and $P_d$, respectively. The characteristics points specified on the left lateral position reference volume data are denoted as $P_a''$, $P_b''$, $P_c''$ and $P_d''$, respectively. Of these characteristics points, $P_a$ and $P_a''$, $P_b$ and $P_b''$, $P_c$ and $P_c''$, and $P_d$ and $P_d''$ respectively represent anatomically the same positions.

Positions of these characteristics points on the oblique coordinates can be represented, in oblique coordinate systems $P_0$-ijk and $P_0''$-i"j"k" set on respective volume data in step S15, as shown in the following Eqs. 22 and 23.

$$\overrightarrow{P_0 P_a} = a_1 i + a_2 j + a_3 k$$
$$\overrightarrow{P_0 P_b} = b_1 i + b_2 j + b_3 k$$
$$\overrightarrow{P_0 P_c} = c_1 i + c_2 j + c_3 k$$
$$\overrightarrow{P_0 P_d} = d_1 i + d_2 j + d_3 k$$
[Eq. 22]

$$\overrightarrow{P_0'' P_a''} = a_1'' i'' + a_2'' j'' + a_3'' k''$$
$$\overrightarrow{P_0'' P_b''} = b_1'' i'' + b_2'' j'' + b_3'' k''$$
$$\overrightarrow{P_0'' P_c''} = c_1'' i'' + c_2'' j'' + c_3'' k''$$
$$\overrightarrow{P_0'' P_d''} = d_1'' i'' + d_2'' j'' + d_3'' k''$$
[Eq. 23]

By the way, it is considered that location of each viscus relative to a skeleton of a human body varies depending on body positions because gravitational direction for each viscera varies. Accordingly, based on the four points specified in step S17, a transformation equation is calculated to transform position of the main blood vessel in the artery system on the supine position reference volume data to position of the main blood vessel in the artery system on the left lateral position reference volume data, so as to formulate personal difference in viscus position depending on the body position (step S18).

Means for the formulation in step S18 will be described below.

To suppose that a random point R on the main blood vessel in the artery system on the supine position reference volume data is at a specific position with respect to a triangular pyramid $P_a P_b P_c P_d$, it can be assumed that a point R" at an equivalent position with respect to a triangular pyramid $P_a"P_b"P_c"P_d"$ on the left lateral position reference volume data corresponds to the same point as the point R on the main blood vessel in the artery system. Under this assumption, the following Eqs. 24 and 25 using proper real numbers a, b and c hold.

$$\overrightarrow{P_a R} = a\overrightarrow{P_a P_b} + b\overrightarrow{P_a P_c} + c\overrightarrow{P_a P_d} \quad [\text{Eq. 24}]$$

$$\overrightarrow{P_a" R"} = a\overrightarrow{P_a" P_b"} + b\overrightarrow{P_a" P_c"} + c\overrightarrow{P_a" P_d"} \quad [\text{Eq. 25}]$$

Here, if directional components of a position vector $P_a R$ of the point R in oblique coordinate axes i, j, k are defined as $x_R$, $y_R$, $z_R$, respectively, then the following Eq. 26 holds.

$$\overrightarrow{P_0 R} = x_R i + y_R j + z_R k \quad [\text{Eq. 26}]$$

Similarly, if directional components of a position vector $P_a"R"$ of the point R" in oblique coordinate axes i", j", k" are defined as $x_R"$, $y_R"$, $z_R"$, respectively, then the following Eq. 27 holds.

$$\overrightarrow{P_0" R"} = x_R" i" + y_R" j" + z_R" k" \quad [\text{Eq. 27}]$$

In the following, based on the above-described equations, position vector $P_0"R"$ of the corresponding point R" on the left lateral position reference volume data, and directional components $x_R"$, $y_R"$, $z_R"$ of the corresponding point R" in the oblique coordinate will be determined from the random point R on the supine position reference volume data.

First, expressing the Eq. 24 as a position vector from the origin $P_0$ results in the following Eq. 28.

$$\overrightarrow{P_0 R} - \overrightarrow{P_0 P_a} = \quad [\text{Eq. 28}]$$
$$a(\overrightarrow{P_0 P_b} - \overrightarrow{P_0 P_a}) + b(\overrightarrow{P_0 P_c} - \overrightarrow{P_0 P_a}) + c(\overrightarrow{P_0 P_d} - \overrightarrow{P_0 P_a})$$

Expressing the components of the Eq. 28 using the Eqs. 22 and 26 results in the following Eq. 29.

$$\begin{pmatrix} x_R \\ y_R \\ z_R \end{pmatrix} - \begin{pmatrix} a_1 \\ a_2 \\ a_3 \end{pmatrix} = \begin{pmatrix} b_1 - a_1 & c_1 - a_1 & d_1 - a_1 \\ b_2 - a_2 & c_2 - a_2 & d_2 - a_2 \\ b_3 - a_3 & c_3 - a_3 & d_3 - a_3 \end{pmatrix} \begin{pmatrix} a \\ b \\ c \end{pmatrix} \quad [\text{Eq. 29}]$$

Here, to simply express the following equations, there is defined a 3 by 3 matrix Q shown in the following Eq. 30.

$$Q = \begin{pmatrix} b_1 - a_1 & c_1 - a_1 & d_1 - a_1 \\ b_2 - a_2 & c_2 - a_2 & d_2 - a_2 \\ b_3 - a_3 & c_3 - a_3 & d_3 - a_3 \end{pmatrix} \quad [\text{Eq. 30}]$$

Substitution of the Eq. 30 to the Eq. 29 results in the following Eq. 31.

$$\begin{pmatrix} x_R \\ y_R \\ z_R \end{pmatrix} - \begin{pmatrix} a_1 \\ a_2 \\ a_3 \end{pmatrix} = Q \begin{pmatrix} a \\ b \\ c \end{pmatrix} \quad [\text{Eq. 31}]$$

Thus, multiplying an inverse matrix of the matrix Q on both sides of the Eq. 31 from the left results in the following Eq. 32.

$$\begin{pmatrix} a \\ b \\ c \end{pmatrix} = Q^{-1} \left\{ \begin{pmatrix} x_R \\ y_R \\ z_R \end{pmatrix} - \begin{pmatrix} a_1 \\ a_2 \\ a_3 \end{pmatrix} \right\} \quad [\text{Eq. 32}]$$

Meanwhile, expressing the Eq. 25 as a position vector from the origin $P_0"$ results in the following Eq. 33, as the Eq. 24 resulted in the Eq. 28.

$$\overrightarrow{P_0" R"} - \overrightarrow{P_0" P_a"} = \quad [\text{Eq. 33}]$$
$$a(\overrightarrow{P_0" P_b"} - \overrightarrow{P_0" P_a"}) + b(\overrightarrow{P_0" P_c"} - \overrightarrow{P_0" P_a"}) + c(\overrightarrow{P_0" P_d"} - \overrightarrow{P_0" P_a"})$$

Furthermore, expressing the components of the Eq. 33 using the Eqs. 23 and 27 results in the following Eq. 34, as applying the Eqs. 22 and 26 to the Eq. 28 resulted in the Eq. 29.

$$\begin{pmatrix} x_R" \\ y_R" \\ z_R" \end{pmatrix} - \begin{pmatrix} a_1" \\ a_2" \\ a_3" \end{pmatrix} = \begin{pmatrix} b_1" - a_1" & c_1" - a_1" & d_1" - a_1" \\ b_2" - a_2" & c_2" - a_2" & d_2" - a_2" \\ b_3" - a_3" & c_3" - a_3" & d_3" - a_3" \end{pmatrix} \begin{pmatrix} a \\ b \\ c \end{pmatrix} \quad [\text{Eq. 34}]$$

Here also, to simply express the following equations, there is defined a 3 by 3 matrix Q" shown in the following Eq. 35.

$$Q" = \begin{pmatrix} b_1" - a_1" & c_1" - a_1" & d_1" - a_1" \\ b_2" - a_2" & c_2" - a_2" & d_2" - a_2" \\ b_3" - a_3" & c_3" - a_3" & d_3" - a_3" \end{pmatrix} \quad [\text{Eq. 35}]$$

Substitution of the Eq. 35 to the Eq. 34 results in the following Eq. 36.

$$\begin{pmatrix} x_R" \\ y_R" \\ z_R" \end{pmatrix} - \begin{pmatrix} a_1" \\ a_2" \\ a_3" \end{pmatrix} = Q" \begin{pmatrix} a \\ b \\ c \end{pmatrix} \quad [\text{Eq. 36}]$$

Because a, b and c in the right side of the Eq. 36 is defined by the above-described Eq. 32, substitution of the Eq. 32 to the Eq. 36 results in the following Eq. 37.

$$\begin{pmatrix} x_R'' \\ y_R'' \\ z_R'' \end{pmatrix} - \begin{pmatrix} a_1'' \\ a_2'' \\ a_3'' \end{pmatrix} = Q''Q^{-1}\left\{ \begin{pmatrix} x_R \\ y_R \\ z_R \end{pmatrix} - \begin{pmatrix} a_1 \\ a_2 \\ a_3 \end{pmatrix} \right\} \quad \text{[Eq. 37]}$$

Therefore, the following Eq. 38 is obtained.

$$\begin{pmatrix} x_R'' \\ y_R'' \\ z_R'' \end{pmatrix} = \begin{pmatrix} a_1'' \\ a_2'' \\ a_3'' \end{pmatrix} + Q''Q^{-1}\left\{ \begin{pmatrix} x_R \\ y_R \\ z_R \end{pmatrix} - \begin{pmatrix} a_1 \\ a_2 \\ a_3 \end{pmatrix} \right\} \quad \text{[Eq. 38]}$$

Thus, using the Eqs. 27 and 38, the position vector $P_0''R''$ of the corresponding point R" on the left lateral position reference volume data, and the directional components $x_R''$, $y_R''$, $z_R''$ of the corresponding point R" in the oblique coordinate are determined from the random point R on the supine position reference volume data.

Thus was formulated the relation between the main blood vessel in the artery system on the supine position reference volume data and the main blood vessel in the artery system on the left lateral position reference volume data.

When the above-described processing of step S18 ends, processing in step S19 is performed next. That is, based on the relation equation (difference in viscus position depending on body position) between the main blood vessel in the artery system on the supine position reference volume data and the main blood vessel in the artery system on the left lateral position reference volume data, calculated in the above-described step S18, the main blood vessel in the artery system on the subject's own supine position volume data is corrected to a position of the main blood vessel in the artery system of when the subject is brought into the left lateral position, thus producing the subject's own supine position volume data (step S19).

Details of the processing in step S19 is described below.

First, an oblique coordinate system $P_0'$-i'j'k' on the subject's own supine position volume data calculated in step S15 is used to express position of a pixel R' of the main blood vessel in the artery system on the subject's own supine position volume data extracted in step S16, as shown in following Eq. 39.

$$\overline{P_0'R'} = x_R' i' + y_R' j' + z_R' k' \quad \text{[Eq. 39]}$$

Also, an oblique coordinate system $P_0'$-i'j'k' is used to express a position R''', obtained by correcting the pixel R' to a position of when the subject is brought into the left lateral position, as shown in the following Eq. 40.

$$\overline{P_0'R'''} = x_R''' i' + y_R''' j' + z_R''' k' \quad \text{[Eq. 40]}$$

Then, the above-described Eq. 38 is replaced as shown in the following Eq. 41.

$$\begin{pmatrix} x_R''' \\ y_R''' \\ z_R''' \end{pmatrix} = \begin{pmatrix} a_1'' \\ a_2'' \\ a_3'' \end{pmatrix} + Q''Q^{-1}\left\{ \begin{pmatrix} x_R' \\ y_R' \\ z_R' \end{pmatrix} - \begin{pmatrix} a_1 \\ a_2 \\ a_3 \end{pmatrix} \right\} \quad \text{[Eq. 41]}$$

Next, substitution of $x_R'$, $y_R'$, $z_R'$ to the Eq. 41 can calculate positions $x_R'''$, $y_R'''$, $z_R'''$ of the pixel R' of when the subject is brought into the left lateral position.

To the thus calculated positions $x_R'''$, $y_R'''$, $z_R'''$, pixel value of R" is alloted.

Performing such processings to all pixels configuring an image of the main blood vessel in the artery system completes a subject's own left lateral position three-dimensional image of the main blood vessel in the artery system.

Thereafter, it is determined whether or not the processings of steps S16 to S19 are completed for all regions desired to be displayed on the guide image (step S20). In the present embodiment, it is assumed that regions to be used for the guiding are the main blood vessel in the artery system, the main blood vessel in the portal system, the pancreas, the gallbladder, the liver, the lien, and the kidney, as mentioned above. Therefore, if this step S20 determines that the processings are not complete for all the regions, then the procedure returns to step S16 to repeatedly perform the above-described processings of steps S16 to S19 to any unprocessed region of the seven kinds of viscera or organs, changing the regions.

Thus, if step S20 determines that the processings are complete for all the regions, then is complete the three-dimensional image of the extracted specific viscera or organs of the subject himself/herself in the left lateral position, which ends this processing.

According to such second embodiment, even if the subject's body position of when performing an inspection with the ultrasonic endoscope 2 is different from the subject's body position of when the MDCT data was picked up, positions of viscera or organs on the guide image can be changed in line with subject's body position. This allows the positional relation between the ultrasonic scanning surface and peripheral viscera or organs on the guide image to accurately agree with the actual positional relation between the ultrasonic endoscope 2 and viscera or organs, which leads to quick approach to a region of interest such as a diseased part, contributing to shorten inspection time.

Moreover, because positions of the viscera or organs in the MDCT data photographed in the supine position can be corrected to those in the left lateral position, the need is eliminated to pick up MDCT data in the left lateral position for guiding in the inspection with the ultrasonic endoscope 2. In other words, a normally photographed CT data in the supine position can be used for guiding in the inspection with the ultrasonic endoscope 2, which permits reducing preparation burden on the subject and the operator.

In addition, in some cases in inspection with the ultrasonic endoscope 2, the ultrasonic transducer 21 is put in water accumulated in the tube cavity to obtain an ultrasonic image, because ultrasonic wave attenuates in air. At this time, the subject's body position is in some cases changed during inspection to facilitate accumulating the water in the tube cavity. Even in such a case, viscera positions in a guide image can be advantageously corrected in line with the body position during inspection, by inputting body position information.

Furthermore, viscera or organs are corrected based on a body position in a divided manner for each region thus allowing optimum correction for each viscus or organ, even if personal difference in location and size exists for each viscus or organ. In this manner, the accurate agreement is rendered possible between the positional relation between the ultrasonic scanning surface and peripheral viscera or organs on the guide image, and the actual positional relation between the ultrasonic endoscope 2 and viscera or organs.

In addition, by applying the transformation equation to each pixel in the supine position CT image of the subject to be inspected with the ultrasonic endoscope 2, thereby reflecting gravitational influence on locations of viscera or organs due to body position change, it is rendered possible to reproduce shape and diseased part specific to the subject himself/herself on the viscera or organs on the guide image, despite a significant personal difference in shape of viscus or organ or diseased part. This results in accurate agreement between actual shapes of viscera or organs on the ultrasonic image and shapes of viscera or organs on the guide image.

Moreover, because each pixel value on the supine position CT image of the subject himself/herself to be inspected with the ultrasonic endoscope 2 is displayed as-is on the guide image, it is possible to compare a diseased part of the subject himself/herself with the ultrasonic image. This provides accurate agreement between actual shapes of viscera or organs on the ultrasonic image and shapes of viscera or organs on the guide image.

Also, even in positioning between an ultrasonic image and an anatomical three-dimensional image, it is possible to produce two-dimensional tomographic image data from a body-position-corrected anatomical three-dimensional image and specify characteristics points on the produced two-dimensional tomographic image data. This provides accurate agreement between the positional relation between the ultrasonic scanning surface and peripheral viscera or organs on the guide image, and the actual positional relation between the ultrasonic endoscope 2 and viscera or organs.

Note that, instead of the subject's own MDCT data, a subject's own MRI or ultrasonic image may be used as subject's own medical image data, as in the above-described first embodiment.

Likewise, instead of the reference MDCT data, an MRI or ultrasonic image of a different person other than the subject, or a viscera model produced from a mean value of data of a plurality of persons (group of other subjects) may be used as reference medical image data, as in the above-described first embodiment.

Also, the medical instrument to be guided may be a laparoscope or treatment instrument, as in the above-described first embodiment.

Furthermore, the transformation equation for correcting the position of each viscus or organ may be calculated using a pseudo inverse matrix, on the basis of, for example, two sets of multiple point groups respectively specified on the viscera in the two kinds of volume data, as in the above-described first embodiment.

In addition, in the present embodiment, the image storing section 52 of the guide image producing device 5 preserves reference MDCT data of various body positions, and based on the MDCT data, the body position correcting section 53 calculates, for each viscus or organ, a transformation equation for providing a displacement unique to a body position. However, the present embodiment is not limited to such a configuration. For example, a transformation equation for a body position for each viscus or organ may be calculated and produced in advance based on MDCT data for each body position, and the calculated transformation equation may be retained in the body position correcting section 53. Adopting such a configuration eliminates the need for the body position correcting section 53 to analyze reference MDCT data, allowing body position correction processing to be performed faster.

Note that, although the above-described embodiments were described mainly regarding the medical guiding system, the present invention is not limited thereto and may also be applied to a medical guiding program or medical guiding method for performing similar processings using a computer.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical guiding system, comprising:
    detecting means for detecting position and orientation of a medical instrument;
    preserving means for preserving medical image data obtained before use of the medical instrument;
    correcting means for correcting, in the medical image data, at least one of position and direction of at least one of a viscus and an organ, in accordance with body position of a subject; and
    calculating means for calculating position of the medical instrument in the medical image data corrected by the correcting means, based on at least one of position and orientation of the medical instrument detected by the detecting means, wherein
    the preserving means preserves therein as the medical image data:
        subject's own medical image data of the subject himself/herself obtained before use of the medical instrument,
        first reference medical image data obtained before use of the medical instrument, from another subject in the same body position as that of the subject when the subject's own medical image data was obtained, and
        second reference medical image data obtained before use of the medical instrument, from the another subject in a body position different from that of the subject when the subject's own medical image data was obtained, and
    the correcting means calculates, based on the subject's own medical image data and the first reference medical image data, a displacement of at least one of position and direction of at least one of a viscus and an organ, the correcting means correcting, based on the calculated displacement, at least one of position and direction of at least one of a viscus and an organ of the second reference medical image data.

2. The medical guiding system according to claim 1, wherein the correcting means performs the correction for each viscus and organ to be displayed on a guide image.

3. The medical guiding system according to claim 1, wherein the body position different from that of the subject of when the subject's own medical image data was obtained, is the same body position as a body position of the subject during use of the medical instrument.

4. The medical guiding system according to claim 1, wherein the calculating means calculates position of the medical instrument in the medical image data corrected by the correcting means, based on the position and orientation of the medical instrument detected by the detecting means.

5. A medical guiding system comprising:
  detecting means for detecting position and orientation of a medical instrument;
  preserving means for preserving medical image data obtained before use of the medical instrument;
  correcting means for correcting, in the medical image data, at least one of position and direction of at least one of a viscus and an organ, in accordance with body position of a subject; and
  calculating means for calculating position of the medical instrument in the medical image data corrected by the correcting means, based on at least one of position and orientation of the medical instrument detected by the detecting means, wherein
    the preserving means preserves subject's own medical image data of the subject himself/herself obtained as the medical image data before use of the medical instrument; and
    the correcting means holds therein displacement due to difference in body position, the displacement being at least one of position and direction of at least one of a viscus and an organ, calculated based on reference medical image data of another subject, the correcting means correcting, in accordance with a body position, at least one of position and direction of at least one of a viscus and an organ in the subject's own medical image data, based on the displacement.

6. The medical guiding system according to claim 5, wherein the correcting means performs the correction for each viscus and organ to be displayed on a guide image.

7. The medical guiding system according to claim 5, wherein
  the preserving means further preserves therein as the medical image data,
    first reference medical image data obtained before use of the medical instrument, from the another subject in the same body position as that of the subject of when the subject's own medical image data was obtained, and
    second reference medical image data obtained before use of the medical instrument, from the another subject in a body position different from that of the subject of when the subject's own medical image data was obtained, and
  the correcting means calculates, based on the first reference medical image data and the second reference medical image data, displacement due to difference in body position, the displacement being of at least one of position and direction of at least one of a viscus and an organ, obtained from the another subject, and then holds the calculated displacement.

8. The medical guiding system according to claim 7, wherein the body position different from that of the subject of when the subject's own medical image data was obtained, is the same body position as a body position of the subject during use of the medical instrument.

9. A non-transitory computer readable storage medium storing a medical guiding program of instructions executable by a computer, said program causing the computer to:
  detect position and orientation of a medical instrument;
  preserve medical image data obtained before use of the medical instrument;
  correct at least one of position and direction of at least one of a viscus and an organ in the medical image data, in line with a body position of a subject; and
  calculate position of the medical instrument in the medical image data obtained by the correction, based on a position of the medical instrument obtained by the detection, wherein
  the medical image data preserved comprises:
    subject's own medical image data of the subject himself/herself obtained before use of the medical instrument,
    first reference medical image data obtained before use oh the medical instrument, from another subject in the same body position as that of the subject when the subject's own medical image data was obtained, and
    second reference medical image data obtained before use of the medical instrument, from the another subject in a body position different from that of the subject when the subject's own medical image data was obtained, and
  the calculate is performed, based on the subject's own medical image data and the first reference medical image data, using a displacement of at least one of position and direction of at least one of a viscus and an organ, the correction is performed, based on the calculated displacement, using at least one of position and direction of at least one of a viscus and an organ of the second reference medical data.

10. A medical guiding method, comprising:
  detecting position and orientation of a medical instrument;
  preserving medical image data obtained before use of the medical instrument;
  correcting at least one of position and direction of at least one of a viscus and an organ in the medical image data, in line with a body position of a subject; and
  calculating position of the medical instrument in the medical image data obtained by the correction, based on a position of the medical instrument obtained by the detection, wherein
  the step of preserving, preserves therein as the medical image data:
    subject's own medical image data of the subject himself/herself obtained before use of the medical instrument,
    first reference medical image data obtained before use of the medical instrument, from another subject in the same body position as that of the subject when the subject's own medical image data was obtained, and
    second reference medical image data obtained before use of the medical instrument, from the another subject in a body position different from that of the subject when the subject's a own medical image data was obtained, and
  the step of calculating calculates, based on the subject's own medical image data and the first reference medical image data, a displacement of at least one of position and direction of at least one of a viscus and an organ, the step of correcting is performed, based on the calculated displacement, using at least one of position and direction of at least one of a viscus and an organ of the second reference medical image data.

* * * * *